United States Patent [19]

Wilhelmy

[11] Patent Number: 5,722,977

[45] Date of Patent: Mar. 3, 1998

[54] METHOD AND MEANS FOR ANTERIOR LUMBAR EXACT CUT WITH QUADRILATERAL OSTEOTOME AND PRECISION GUIDE/SPACER

[75] Inventor: John K. Wilhelmy, Diablo, Calif.

[73] Assignee: Danek Medical, Inc., Memphis, Tenn.

[21] Appl. No.: 590,612

[22] Filed: Jan. 24, 1996

[51] Int. Cl.$^6$ .................................................. A61B 17/16
[52] U.S. Cl. .................................................. 606/84; 606/61
[58] Field of Search .................................. 606/79, 84, 87; 623/17; 144/70, 75, 78; 408/30

[56] References Cited

U.S. PATENT DOCUMENTS

| | | | |
|---|---|---|---|
| 1,279,495 | 9/1918 | Dom | 408/204 |
| 1,401,469 | 12/1921 | Hawkinson | 408/30 |
| 3,683,892 | 8/1972 | Harris | 128/754 |
| 3,848,601 | 11/1974 | Ma et al. | 606/61 |
| 5,423,825 | 6/1995 | Levine | 606/86 |

*Primary Examiner*—Michael Buiz
*Assistant Examiner*—David O. Reip

*Attorney, Agent, or Firm*—John J. Leavitt

[57] ABSTRACT

Presented is a method and instrumentation for removal of a pair of rectangular blocks of vertebral bone tissue of predetermined and precise dimensions to provide an intervertebral recess, with guarded depth for safety, achieving and maintaining the desired intervertebral space, as well as obtaining and injecting into the intervertebral recess a well-fitted bone plug of the same dimension as the recess that receives it. Two cooperating instruments are utilized in the invention, one being an intervertebral mortising cutter and the other a precision guide and spacer. The guide and spacer functions dually to retain the associated adjacent vertebrae at a precise selected and predetermined spacing and to guide penetration of the mortising cutter. Following advancement of the mortising cutter into the bone tissue of the two adjacent vertebrae, the instruments, along with the blocks of bone tissue, are removed from the site to produce a precisely configured recess. The mortising cutter is then used to harvest a bone plug from a suitable donor site, with the bone plug being subsequently inserted into the prepared vertebral recess to thus promote fusion between the bone plug and the associated surfaces of the vertebrae.

16 Claims, 4 Drawing Sheets

METHOD AND MEANS FOR ANTERIOR LUMBAR EXACT CUT WITH QUADRILATERAL OSTEOTOME AND PRECISION GUIDE/SPACER

BACKGROUND OF THE INVENTION

1. Field of the Invention

This invention relates to a method and a means for effecting an exact cut in adjacent vertebrae in preparation for fusion of the adjacent vertebrae, and particularly to an osteotome having a quadrilateral cutting edge manipulable in cooperation with a precision guide spacer to provide the exact cut and to retain the adjacent vertebrae properly spaced pending the insertion of a bone plug in the recess thus formed between the adjacent vertebrae.

2. Description of the Prior Art

A preliminary patentability and novelty search in connection with this invention has revealed the existence of U.S. Pat. Nos. 1,279,495, 3,683,892 and 3,848,601.

It has been become a relatively common practice to perform both anterior and posterior approach interbody fusion of adjacent vertebrae. The need for the procedure may arise from trauma to the spine because of an accident that results in more or less severe compression and/or fracture of one or more vertebrae that causes interminable and disabling pain. The need for interbody fusion of vertebrae may also arise from the progression of spinal stenosis resulting from osteoarthritis. Excessive use, previous injury or aging, slowly deteriorates the protective tissue (cartilage) covering joint surfaces in the spine. Discs between the vertebrae become worn and normal spacing between vertebrae narrows. Bony outgrowths called "spurs" (osteophytes) also develop. Other indications suggesting the need for vertebral fusion include: severe degenerative disc with or without instability; post traumatic conditions; tumor; congenital defects; and failed previous posterior fusions.

When medication, physical therapy, back supports or corticosteroid injections do not alleviate the condition and lessen the pain, it may become necessary to resort to a surgical procedure called fusion wherein vertebrae, in the lower back for instance, are fused together using a bone graft. Conventionally, bone grafts are often accompanied by rigidifying the graft site through use of metal support devices such as specialized screws and/or plates. The instruments and procedures forming the subject matter of this invention reduce the need for such metal support devices, thus significantly increasing the probability of a more favorable medical outcome and effective vertebral fusion.

It has become customary in anterior lumbar fusion procedures to use osteotomes to remove the cartilaginous surface of the superior plate of the vertebra below and the inferior plate of the vertebra above, at the interspace, to accommodate a rectangular bone graft plug impacted into the interspace, where it is retained by the natural compressive forces exerted on the vertebrae until it fuses to the associated surfaces of the adjacent vertebrae. The conventional techniques and procedures of interbody fusion of vertebrae of the spine are not new, and both the anterior and posterior approach to perform interbody fusion have been known for many years. However, it is extremely difficult upon initiation of these conventional procedures to maintain the proper spacing between adjacent vertebrae from which bone portions are to be removed to create the recess for the subsequent insertion of an accurately cut bone graft plug.

Accordingly, one of the important objects of the present invention is to provide a four-sided osteotome instrument that will simultaneously provide accurate and exact cuts in the surfaces of adjacent vertebrae to form the bone plug recess, and which may also be utilized to "harvest" the bone plug for insertion into the recess.

Another object of the invention is the provision of a disc spreader or guide/spacer device that performs the dual function of guiding the osteotome in its passage into the bone tissue of the vertebrae and which retains the adjacent vertebrae spaced appropriately during the bone-cutting procedure so as to facilitate removal of correspondingly exact amounts of bone tissue from adjacent vertebrae.

Still another object of the invention is the provision, as an article of manufacture, of a precision guide/spacer adapted for use with a four-sided osteotome, the precision guide/spacer being separately insertable between adjacent vertebrae to space the confronting surfaces of the vertebrae to a precise selected dimension.

Yet another object of the invention is to provide a method by which an osteotome having four cutting edges forming a quadrilateral configuration may be used in cooperation with a precision guide/spacer to precisely control the size of the cut, to provide the correct angle of the cut, and to provide a correct depth for the cut, thus injecting a level of precision in this procedure not heretofore available with conventional procedures and instruments.

The invention possesses other objects and features of advantage, some of which, with the foregoing, will be apparent from the following description and the drawings. It is to be understood however that the invention is not limited to the embodiment illustrated and described since it may be embodied in various forms within the scope of the appended claims.

SUMMARY OF THE INVENTION

In terms of broad inclusion, the present invention provides for removal of a pair of rectangular blocks of vertebral bone tissue of predetermined and precise dimensions to provide an intervertebral recess, with guarded depth for safety, achieving and maintaining the desired intervertebral space, as well as obtaining and injecting into the intervertebral recess for fusion therein with safety and in minimum time a well-fitted bone plug of the same dimension as the recess that receives it. With the apparatus of the invention, interbody fusion of the spine, utilizing the anterior or lateral approach, are greatly facilitated. Accordingly, the invention is described herein as it applies to the anterior or lateral approach procedure.

Structurally, the instant invention includes two cooperating instruments, an intervertebral mortising cutter and a precision guide/spacer, the latter functioning dually to retain the associated adjacent vertebrae at a precise selected and predetermined spacing to suit the patient's intervertebral disc space and to guide penetration of the mortising cutter. Following advancement of the mortising cutter into the bone tissue of the two adjacent vertebrae, directed by the guide/spacer, an appropriate distractor instrument (not shown) may be utilized to maintain the selected spacing between and alignment of the associated vertebrae, and the intervertebral mortising cutter and precision guide/spacer, together with the two rectangular blocks of bone tissue, are removed from the site to produce a precisely configured recess, so that an appropriately sized bone plug, "harvested" by use of the mortising cutter unit in a suitable donor site, may be inserted into the prepared recess between the adjacent vertebrae to thus promote fusion between the bone plug and the associated surfaces of the vertebrae.

It will of course be understood that it is common to "harvest" the bone plug from the iliac crest. The "harvested" bone plug is injected into the intervertebral recess utilizing a conventional properly sized bone plug injector instrument (not shown). While it is preferred that a single monolithic bone plug be inserted between the associated vertebrae, the invention contemplates the insertion of two laterally spaced bone plugs, of the same chosen dimension, injected for grafting into the desired intervertebral space. The method and apparatus is preferably used for anterior approach interbody fusion as well as for many other procedures in which a specified dimension of bone plug is to be "harvested" from an appropriate site, and utilized when a rectangular bone graft of the same dimension is dictated by need. Alternatives to solid iliac crest bone grafts include cages, packed with donor bone, allografs, or possible bone substitutes with biochemical fusion enhancement substances (i.e., bone morphagenic proteins).

DESCRIPTION OF A PREFERRED EMBODIMENT

In the interest of brevity in this description, suffice to say that the invention described and illustrated herein is intended for use in connection with an anterior approach to the traumatized spine. The specific surgical procedure utilized by the surgeon to approach the anterior surface or area of the spine is purposely omitted for the reason that the surgical procedure in general is well known and varys from patient-to-patient depending upon the specific area of the spine to be approached and the nature of the trauma to be repaired. While the invention herein described and illustrated will be explained in relation to an anterior approach, it should be understood that under appropriate circumstances the invention may also be used in conjunction with a lateral approach.

Figure 1:
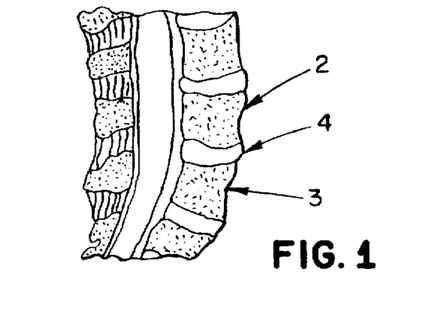
FIG. 1 is a fragmentary vertical cross-sectional view of a portion of a spine illustrating four associated vertebrae as they might appear in a non-traumatized condition.
Figure 2:
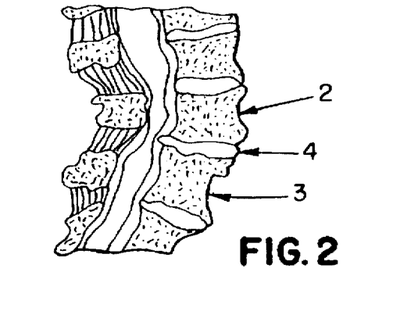
FIG. 2 is a vertical cross-sectional view similar to FIG. 1, but showing how a displaced disc and a ligament folded inwardly may result in compression of the spinal canal and apply pressure on spinal nerves, thus suggesting the need for intervertebral fusion.
Figure 3:
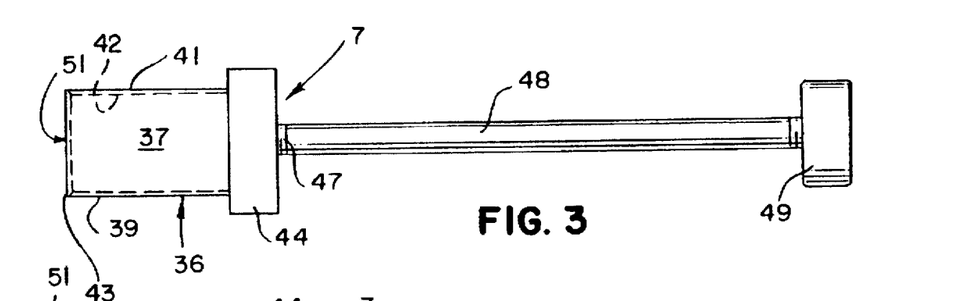
FIG. 3 is a top plan view of a four-sided osteotome or motising chisel.

FIG. 1 illustrates in side elevation a fragmentary portion of a spinal column and shows an upper vertebra 2 and a lower vertebra 3 separated by a spinal disc 4. This view illustrates diagrammatically the relative positions of some of the components of a non-traumatized spinal column. FIG. 2 is a side elevational view of the same portion of the spinal column, but illustrating the shifted positions of the components as a consequence of trauma, thus suggesting the need for intervertebral fusion of the adjacent vertebrae by insertion of an appropriate bone graft plug in the intervertebral space normally occupied by the disc.

Figures 18, 19, 20, 21:
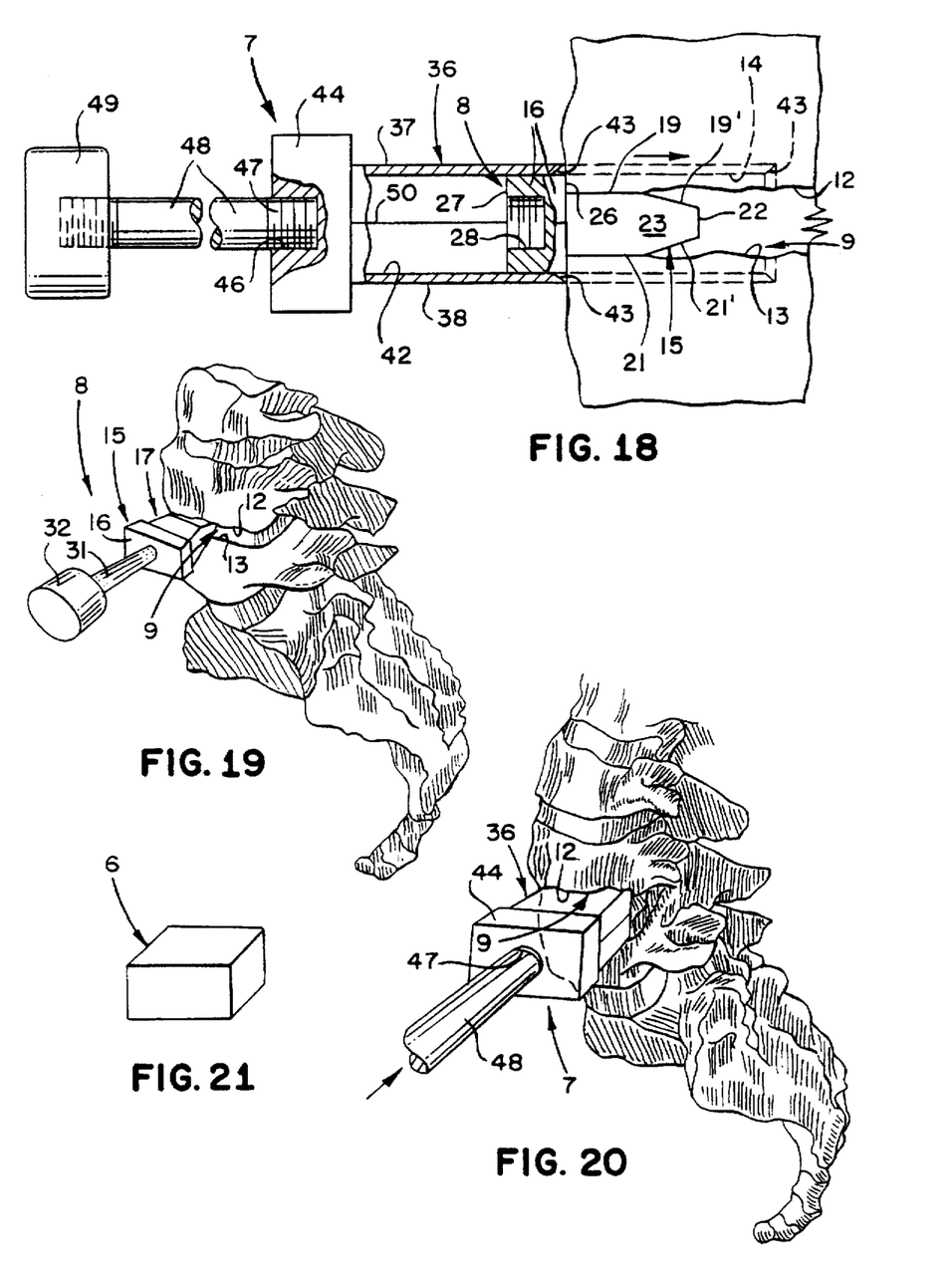
FIG. 18 is a fragmentary side elevational diagrammatic view illustrating the relationship between two adjacent vertebrea and the application of the four-sided osteotome of FIG. 3 surrounding and guided by the in-place precision guide/spacer of FIG. 8 for the purpose of effecting a precise cut in the two adjacent vertebrae. Portions of the osteotome and the precision guide/spacer head are shown in cross-section in the interest of clarity.
FIG. 19 is a fragmentary perspective view of several vertebrae and illustrating the method and means of anterior placement of the precision guide/spacer instrument in relation to the intervertebral space prior to the spacer being driven thereinto.
FIG 20 is a view similar to FIG. 19, illustrating the four-sided osteotome circumscribed about the in-place head of the precision guide/spacer instrument.
FIG. 21 is a perspective view illustrating the configuration of a bone plug secured from an appropriate bone graft site, for instance the iliac, and prepared for insertion into the recess formed by the four-sided osteotome so as to effect fusion of the bone plug with the adjacent vertebrae.

To provide a recess for a bone plug 6 as illustrated in FIG. 21, the four-sided osteotome illustrated in FIGS. 3–7 and designated generally by the numeral 7, is applied to the spinal column, preferably anteriorly, in the manner illustrated in FIGS. 16–18 and 20, following insertion of the precision guide/spacer instrument, designated generally by the numeral 8, into the intervertebral space 9 defined between the two adjacent inferior and superior surfaces 12 and 13, respectively, of the upper and lower vertebrae, as illustrated in FIGS. 15-20. The vertebral disc 4 may be totally or partially excised by conventional means as needed, utilizing conventional procedures. It should be noted however that the precision guide/spacer instrument 8 may be inserted into the intervertebral space 9 without first excising the vertebral disc 4. Alternatively, the vertebral disc 4 may be excised either partially or totally prior to insertion of the precision guide/spacer instrument into the intervertebral space 9.

After proper separation of the confronting inferior and superior surfaces 12 and 13 of the adjacent vertebrae by application of the precision guide/spacer instrument 8 therebetween, the confronting surfaces of the two vertebrae are retained thus properly spaced by the head of the guide/spacer to facilitate application of the four-sided osteotome about the guide/spacer head which stabilizes and guides the four-sided osteotome in making a precise cut in the opposed vertebrae parallel to the opposed inferior and superior surfaces thereof and to a predetermined and precise depth to form the precisely formed and dimensioned recess into which the bone plug 6 (FIG. 21) is to be inserted.

It should be understood that the drawings illustrate the osteotome being applied to the anterior surface of the spinal column, and in most instances is applied symmetrically in relation to the inferior and superior surfaces, causing equal amounts of bone to be cut from each and avoiding angled cuts which take too much bone from one vertebra and too little bone from the other opposed vertebra. Thus, an inferior portion of the inferior facet of the upper vertebra is removed, and a superior portion of the superior facet of the adjacent lower vertebra is also removed to provide a cavity or recess 14 for the reception of the bone plug. By way of example, the recess in each of the inferior and superior surfaces 12 and 13 of opposed vertebrae may be cut to a precise depth of two millimeters (2 mm), thus enabling placement of a bone plug 6 that is precisely as thick as the predetermined proper intervertebral space for the particular patient, plus four millimeters (4 mm) to thus precisely fit the recess formed for it and thus maintain the proper intervertebral space for the particular patient.

Referring now to the individual instruments illustrated, reference is made to FIGS. 8-15, 18 and 19 of the drawings wherein the precision guide/spacer instrument 8 is seen to include a head portion designated generally by the numeral 15, and comprising a generally rectangular posterior base or guide portion 16, formed integrally with an anteriorly projecting and symmetrical centrally disposed and elongated cantilever-like tapered wedge member designated generally by the numeral 17. As shown, the tapered wedge member 17 is preferably symmetrical with respect to a central axis 18, and is formed with parallel top and bottom surface portions 19 and 21, respectively, and top and bottom surface portions 19' and 21' converging anteriorly toward and intercepted by end surface 22 remote from the posterior base 16. The opposed left and right side surfaces 23 and 24, as seen in FIGS. 8-12, are parallel and extend anteriorly from base 16 and are intercepted by the anterior end surface 22. Preferably, the end surface 22 is dimensionally formed approximately one-half the spacing between top surface 19 and bottom surface 21 to facilitate penetration of the tapered end portion of the wedge member into the intervertebral space 9, to effect progressive separation of the opposed verterbrae until the top and bottom surfaces 19 and 21 lie interposed between the inferior and superior surfaces 12 and 13 of the vertabrae. For instance, the end 22 could be formed with a relatively sharp edge (not shown) to facilitate penetration of the guide/spacer head between the opposed surfaces 12 and 13 of the adjacent vertebrae.

The posterior base 16 is provided with a predetermined thickness defined by the anterior surface 26 that is integral with the base of the tapered wedge member 17, and the posterior surface 27 in which is centrally formed a threaded recess 28. The threaded recess 28 is adapted to detachably receive the threaded end 29 of a handle 31 provided with a head 32 preferably threadably mounted on the opposite end of the handle, and which may be struck by a mallet (not shown) to drive the precision guide/spacer tapered wedge portion 17 into the intervertebral space 9 against the resistance to such penetration offered by the opposing surfaces 12 and 13 of the adjacent vertebrae. Alternatively, the posterior base 16 could be equipped with a threaded stud adapted to be engaged by a threaded recess formed in the end of the handle. Additionally, the posterior base 16 may be provided with a handle that constitutes an integral part of the posterior base, projecting posteriorly in a direction opposed to the tapered wedge member 17 and having a predetermined diameter for reasons which will become clear hereinafter. The precision guide/spacer instrument 8, including the handle 31, are preferably fabricated from medical grade stainless steel in various sizes to accommodate the different needs of different patients. For instance, by way of example, and with no intention of limitation, a prototype instrument had an overall length of 8.5", and overall head length of 1.0", with top and bottom surfaces 19 and 21 spaced 0.37" and extending anteriorly 0.40" from the anterior surface 26. The converging surfaces 19' and 21' extended 0.30", leaving a posterior base 0.30" thick. The height of the end surface 22 was 0.21", while the overall width of the member 17 was 0.68". Obviously, different dimensions may be utilized to properly size the precision guide/spacer instrument for use with different patients.

It will thus be understood that the tapered wedge portion of head 17 functions to initially penetrate the intervertebral space 9 commencing with the small dimension end 22. Since the top and bottom surfaces 19' and 21' diverge toward the posterior base 16, as the member 17 of the precision guide/spacer 8 penetrates incrementally deeper into the intervertebral space, the inferior and superior surfaces 12 and 13 of the adjacent vertebrae are correspondingly separated. Maximum spacing between the vertebrae surfaces 12 and 13 is achieved when the top and bottom parallel surfaces 19 and 20 are fully interposed between vertebrae surfaces 12 and 13 and anterior surface 26 of the posterior base 16, which projects 0.08" past the associated top and bottom surfaces 19 and 20, lies contiguously against the associated surfaces of the adjacent vertebrae. It should be understood that the angle of divergence of the surfaces 19' and 21' is sufficiently shallow to eliminate any tendency for the precision guide/spacer to slip rearwardly out of the intervertebral space prior to achieving maximum penetration.

It should also be noted that the height (0.53") and width (0.84") dimensions of the generally rectangular posterior base member closely approximate the dimensional limits of the recess to be cut into the adjacent vertebrae by use of the osteotome 7. In this way, the horizontal and vertical surfaces of the posterior base 16 of the precision guide/spacer instrument 8 function to guide and stabilize the osteotome 7 in cutting dimensionally equal portions from the adjacent vertebrae so that the bone graft plug 6, when inserted into the recess, retains the vertebrae surfaces 12 and 13 properly spaced to conform to the normal spacing that occurs between the various vertebrae, or the spacing determined by the surgeon to be the best for a particular patient.

Referring to FIGS. 3–7 16–18 and 20, the structure and function of the four-sided osteotome 7 can be clearly discerned from these views. Structurally, the four-sided osteotome 7 comprises a cutting head having a quadrilateral tubular cross-section (FIGS. 5 and 6), designated generally by the numeral 36, and including top and bottom blades 37 and 38, respectively, and left and right side blades 39 and 41, respectively, integral with blades 37 and 38. The four blades of the osteotome head 36 therefore define a rectangular cavity 42, with the end edges 43 of the blades sharpened razor-sharp at a 30 degree interior angle so as to facilitate penetration by the blades of the bone surface of the vertebrae with minimum impact force needed on the osteotome in the direction indicated by the arrow by an appropriate mallet (not shown). The four blades 37, 38, 39 and 41 are joined at their ends remote from the cutting edge 43 by a rear wall 44 having a central threaded bore 46 to which the associated end 47 of a handle 48 is threadably attached. The opposite end of the handle is appropriately secured by any suitable means, as by threads or welding, to the driving head 49 upon which one or more mallet blows are delivered to drive the cutting edges 43 into the surfaces of the adjacent verterbrae.

Figure 4:
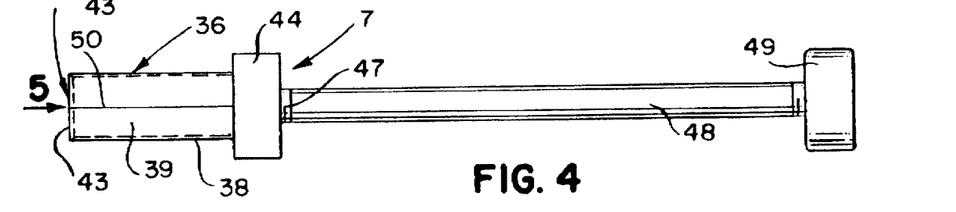
FIG. 4 is a side elevational view of the four-sided osteotome cutter shown in FIG. 3.
Figures 5, 6, 7:
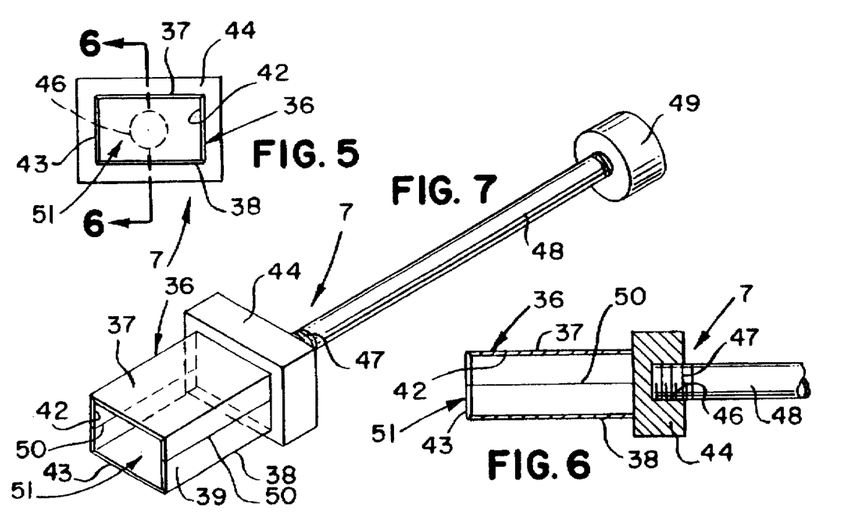
FIG. 5 is an end view of the sharpened cutting edges of the osteotome taken in the direction of the arrow 5 in FIG. 4.
FIG. 6 is a fragmentary vertical cross-sectional view taken in the plane indicated by the line 6—6 in FIG. 5.
FIG. 7 is a perspective view illustrating the four-sided osteotome apart from other instruments.
Figure 8:
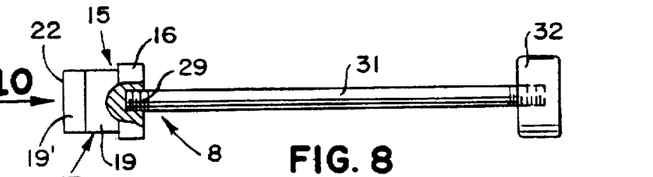
FIG. 8 is a top plan view of the precision guide/spacer instrument, a portion of the structure being broken away to show underlying structure.
Figure 9:
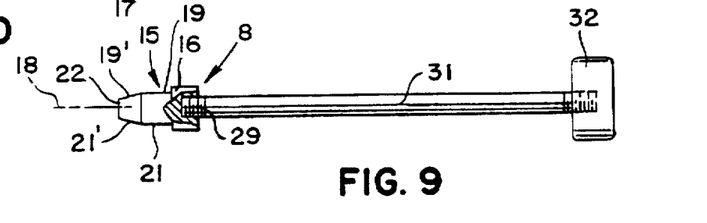
FIG. 9 is a side elevational view of the precision guide/ spacer instrument, a portion of the structure shown in cross-section.
Figure 10:
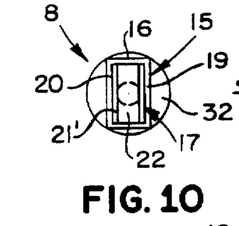
FIG. 10 is an end elevational view of the tapered end of the precision guide/spacer instrument.
Figure 11:
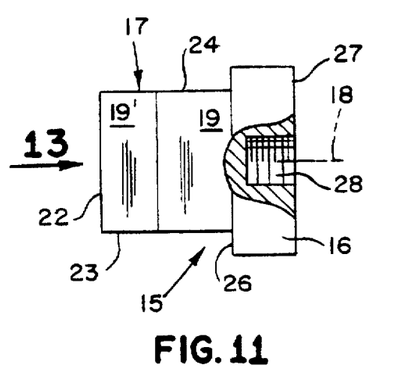
FIG. 11 is an enlarged top plan view of the head of the precision guide/spacer instrument, shown apart from the handle.
Figure 12:
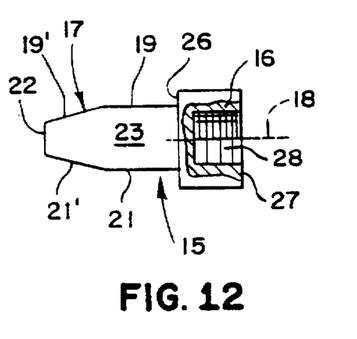
FIG. 12 is an enlarged side elevational view of the head of the precision guide/spacer instrument, shown apart from the handle.
Figure 13:
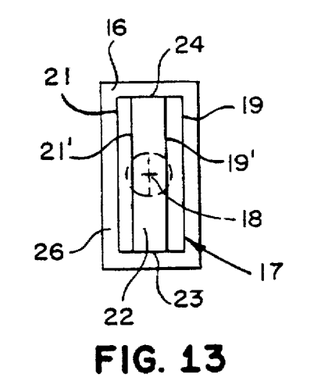
FIG. 13 is an enlarged end elevational view of the head of the precision guide/spacer taken in the direction of the arrow 13 in FIG. 11.
Figure 14:
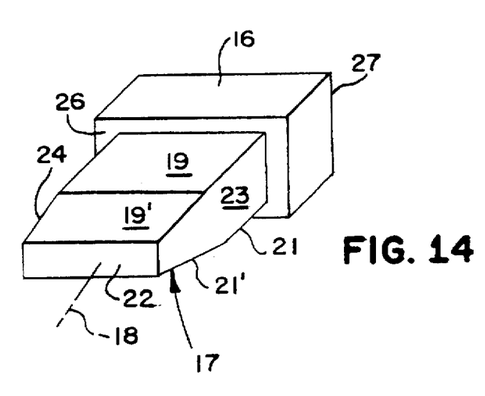
FIG. 14 is an enlarged perspective view of the head of the precision guide/spacer.
Figure 15:
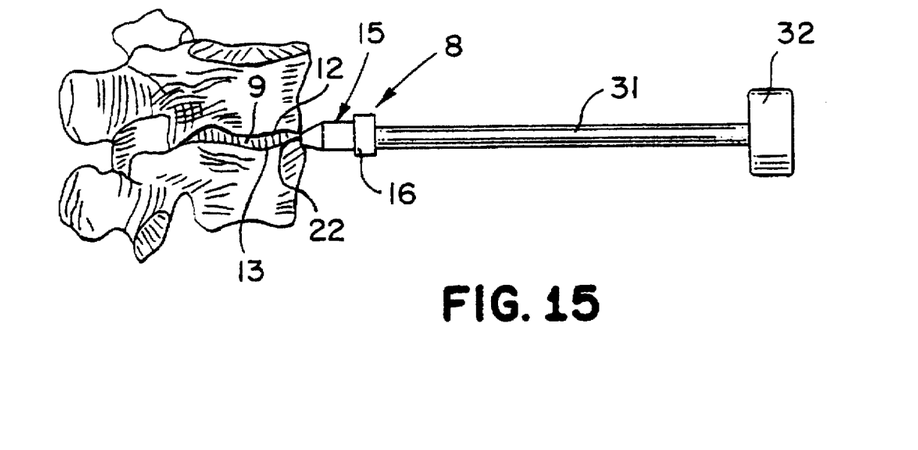
FIG. 15 is a fragmentary side elevational view of two adjacent vertebrae with the precision guide/spacer instrument in position to be impacted and driven into the space between the two vertebrae.
Figure 16:
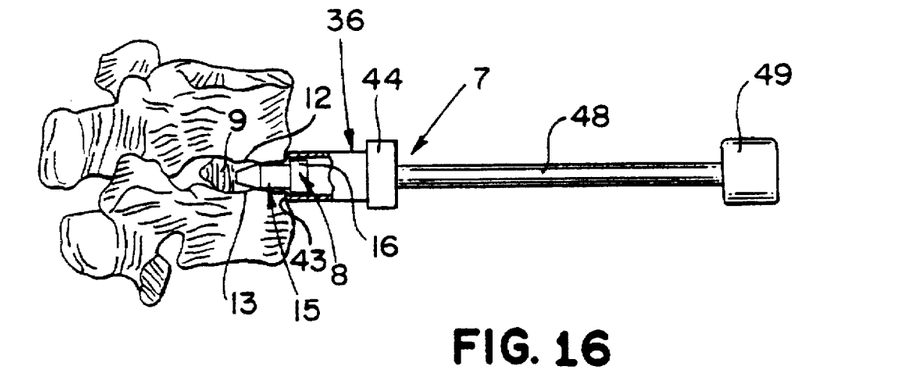
FIG. 16 is a fragmentary side elevational view of two adjacent vertebrae with the precision guide/spacer instrument in final position between the two vertabrae, with the handle removed, and illustrating the initial position of the four-sided osteotome in relation to the precision guide/ spacer head prior to penetration of the vertebrae by the four-sided osteotome to make a precision cut.
Figure 17:
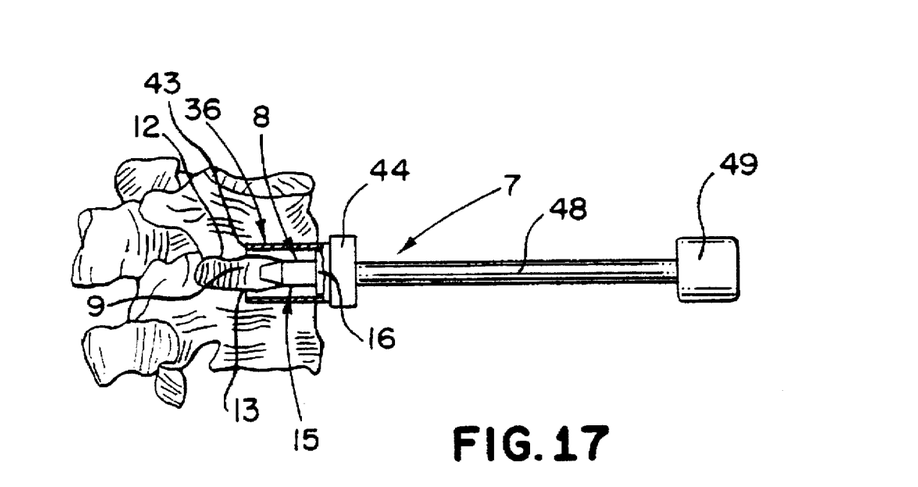
FIG. 17 is a fragmentary side elevational view of two adjacent vertebrae with the precision guide/spacer instrument head in final position in the intervertebral space and illustrating the cutting blades of the four-sided osteotome in full predetermined penetration of the vertebrae to complete the precision cut to form a recess of precise predetermined dimensions.

As illustrated in FIGS. 4 and 6, the tubular cutting head 36 is preferably fabricated from medical grade stainless steel as two separate complementary and mutually facing channels in each of which the parallel top and bottom blades constitute the webs of the channels and the side flanges form blades 39 and 41 which coincide medianly and are welded at 50 to form a unitary rectangular tube with an open end 51 defined by the anterior end edges of the blades, each of which is sharpened to a razor-sharp edge by internally chamferring the end edges at a 30 degree angle to produce the four chisel-shaped sharpened edges 43. The blades 37, 38, 39 and 41 are formed from medical grade stainless steel having a thickness of approximately 0.036" and a length of about 1.57" measured from the anterior surface of the rear wall 44. In a prototype four-sided osteotome, the top and bottom blades 37 and 38 are about 1.10" wide, while the side blades 39 and 41 are about 0.63" in height. The overall length of the four-sided osteotome is about 7.57" The handle 48 is conveniently cylindrical, but may be hollow for the reasons set forth hereinafter.

It is important that the four-sided osteotome edges be driven into the bone surfaces perpendicular to the axis line of the vertabrae. To facilitate such a prerequisite, the cavity 42 of the osteotome head is dimensioned to closely enclose in a snug sliding fit the perimeter of the posterior base 16 of the precision guide/spacer head while providing sufficient clearance therebetween to enable relative movement therebetween while maintaining a close tolerance to ensure accuracy of the cut. To further ensure that this condition of close tolerance prevails, in one embodiment of the invention, the handle 48 of the four-sided osteotome is hollow and provided with an interior diameter that closely matches the exterior diameter of the handle 31 of the precision guide/spacer instrument 8, providing only sufficient clearance so that the handle 31 can slide unobstructed within the hollow interior of handle 48. To facilitate this relationship, the head 32 of the precision guide/spacer instrument 8, being threadably engaged on the end of the handle 31, is therefore removable so that the four-sided osteotome may be telescoped over the handle of the precision guide/spacer instrument to be supported not only by the posterior base 16, but also, when utilized, by the sliding interaction between the handle 31 and the interior of the hollow handle 48. This ensures accurate penetration of the four edges 43 of the osteotome into the bone. Additionally, the precision guide/spacer instrument and osteotome also cooperate in gauging the depth of penetration of the four cutting edges. This is controlled by virtue of the fact that the rear wall 44 of the osteotome head 36 comes into abutting relationship with the surface 27 of the posterior base 16, thus preventing further penetration of the cutting edges. Thus, the depth of the cavity measured between the cutting edges and the inner surface of the rear wall 44 of the head, and the thickness of the posterior base 16, accurately control the depth of penetration of the cutting edges.

Following insertion of the precision guide/spacer instrument, and penetration of the four-sided osteotome cutting edges to the predetermined full depth desired, self-retaining retractors (not shown) may be applied, and the osteotome head and precision guide/spacer assembly, both now embedded in the juxtaposed vertebrae, are gently manipulated incrementally from side-to-side (laterally) and up-and-down (vertically) to sever by fracture the bone tissue in the plane of the cutting edges, thus enabling withdrawal of the instrument assembly with the severed bone sections, the intervertebral disc portions, and the fibrocartilaginous material within the confines of the rectangular recess into which the bone graft plug is to be inserted. Obviously, should some small fragments of any of these tissues remain in the recess, they may be removed by conventional procedures using conventional instruments.

As used herein the expressions "guide/spacer" and "guide and spacer" are intended to be synonymous and relate to a unitary structure that performs both a guiding function and a spacer function.

Having thus described the invention, what is believed to be new and novel and sought to be protected by letters patent of the United States is as follows.

I claim:

1. In combination, a non-rotatable precision guide and spacer means adapted to be driven progressively into an intervertebral space between two juxtaposed vertebrae of a spine to selectively progressively increase the spacing between opposed surfaces of said juxtaposed vertebrae a predetermined amount, and a quadrilateral tubular osteotome surrounding a portion of said precision guide and spacer means and manipulable to simultaneously cut opposed recesses in the juxtaposed spaced vertebrae while spanning the intervertebral space therebetween.

2. The combination according to claim 1, wherein said non-rotatable precision guide and spacer means includes guide means for guiding the penetration of said osteotome into said vertebrae.

3. The combination according to claim 1, wherein said non-rotatable precision guide and spacer means is fabricated from medical grade stainless steel.

4. A precision guide and spacer instrument for use in separating a pair of juxtaposed vertebrae and for guiding the penetration of an osteotome into said vertebrae to form opposed recesses therein, comprising:
   a) a head including a portion adapted to be driven between said pair of juxtaposed vertebrae:
   b) a posterior base portion integral with said head and forming a flange thereabout adapted to abut associated surfaces of said vertebrae to limit penetration of said head portion between said pair of juxtaposed vertebrae: and
   c) a handle secured to said head and extending posteriorly therefrom and adapted to be impacted to drive said head between said vertebrae.

5. The precision guide and spacer instrument according to claim 4, wherein said head includes a tapered wedge portion whereby progressive insertion thereof between said vertebrae effects progressive separation thereof.

6. The precision guide and spacer instrument according to claim 5, wherein said head includes a spacer portion having parallel vertebral support surfaces integrally continuous from said tapered wedge portion whereby said parallel vertebral support surfaces when interposed between said vertebrae define the intervertebral space therebetween.

7. The precision guide and spacer instrument according to claim 6, wherein said head includes a posterior base portion integral with said spacer portion and including a flange projecting laterally from said spacer portion, whereby when said spacer portion is fully disposed between said vertebrae, said flange abuts the lateral surfaces of said juxtaposed vertebrae.

8. The method of forming opposed recesses of equal size and configuration in the opposed inferior and superior surfaces of a pair of juxtaposed vertebrae, comprising the steps of:

a) surgically exposing the anterior surfaces of a pair of juxtaposed vertebrae:

b) driving a precision guide and spacer instrument anteriorly into the intervertebral space between said inferior and superior surfaces of said juxtaposed vertebrae to separate said vertebrae a predetermined amount:

c) abutting a guide portion of said precision guide and spacer instrument against the anterior surfaces of said spaced vertebrae whereby said guide portion equally overlaps anterior surface portions of said spaced vertebrae:

d) superimposing a quadrilateral tubular osteotome circumscribingly about the guide portion of said precision guide and spacer instrument in abutting relation to the anterior surfaces of said spaced vertebrae so that said tubular osteotome overlaps equal anterior portions of said spaced vertebrae:

e) driving said tubular osteotome into said anterior surfaces of said spaced vertebrae to a predetermined depth to cut away equal portions of said inferior and superior surfaces from said spaced vertebrae on opposite sides of said intervertebral space to thereby define said opposed recesses: and f) subsequently extracting said precision guide and spacer instrument, said tubular osteotome and said cut away equal portions of said juxtaposed vertebrae to thereby form said opposed recesses of equal size and configuration.

9. The method according to claim 8, wherein said of precision guide and spacer instrument and tubular osteotome are manipulated following driving of said tubular osteotome into said spaced vertebrae to said predetermined depth to effect disengagement of said osteotome-defined vertebrae portions from the remaining vertebrae to facilitate extraction of said defined vertebrae portions when said precision guide and spacer instrument and said tubular osteotome are extracted.

10. In combination, a precision guide and spacer means adapted to be driven into an intervertebral space between two juxtaposed vertebrae of a spine to selectively space opposed surfaces of said juxtaposed vertebrae a predetermined amount, and a quadrilateral tubular osteotome surrounding a portion of said precision guide and spacer means and manipulable to simultaneously cut opposed recesses in the juxtaposed vertebrae while spanning the intervertebral space therebetween, said precision guide and spacer means including a posterior base portion and a tapered wedge portion.

11. The combination according to claim 10, wherein said posterior base portion is quadrilateral in configuration and wider than said intervertebral space whereby when said precision guide and spacer means is driven between said vertebrae said posterior base portion spans said intervertebral space and normally abuts the associated vertebrae.

12. The combination according to claim 10, wherein said precision guide and spacer means includes a spacer portion having a rectangular cross-section integrally interposed between said posterior base portion and said tapered wedge portion, whereby said tapered wedge portion progressively separates said vertebrae when inserted therebetween and said spacer portion retains said vertebrae in a predetermined spaced relationship while said osteotome is driven into said vertebrae.

13. In combination, a non-rotatable precision guide and spacer means adapted to be driven into an intervertebral space between two juxtaposed vertebrae of a spine to selectively space opposed surfaces of said juxtaposed vertebrae a predetermined amount, and a quadrilateral tubular osteotome surrounding a portion of said precision guide and spacer means and manipulable to simultaneously cut opposed recesses in the juxtaposed vertebrae while spanning the intervertebral space therebetween, said precision guide and spacer means including guide means for guiding the penetration of said osteotome into said vertebrae and including a quadrilateral base portion having an exterior periphery dimensioned to be slidably circumscribed by said quadrilateral tubular osteotome.

14. In combination, a precision guide and spacer means adapted to be driven into an intervertebral space between two juxtaposed vertebrae of a spine to selectively space opposed surfaces of said juxtaposed vertebrae a predetermined amount, and a quadrilateral tubular osteotome surrounding a portion of said precision guide and spacer means and manipulable to simultaneously cut opposed recesses in the juxtaposed vertebrae while spanning the intervertebral space therebetween, said quadrilateral tubular osteotome being open at one end and closed at its other end, said open end having edges sharpened sufficiently to penetrate bone tissue when driven thereagainst and being spaced a predetermined distance from said closed end, said precision guide and spacer means comprising an instrument having a head shorter by a predetermined distance than the distance between said open and closed ends of said osteotome, whereby the difference in length of said precision guide spacer means compared to said osteotome constitutes the depth to which said osteotome will penetrate said vertebrae when driven thereagainst.

15. In combination, a non-rotatable precision guide and spacer means adapted to be driven into an intervertebral space between two juxtaposed vertebrae of a spine to selectively space opposed surfaces of said juxtaposed vertebrae a predetermined amount, and a quadrilateral tubular osteotome surrounding a portion of said precision guide and spacer means and manipulable to simultaneously cut opposed recesses in the juxtaposed vertebrae while spanning the intervertebral space therebetween, said precision guide and spacer means including guide means for guiding the penetration of said osteotome into said vertebrae, and including stop means controlling the maximum depth to which said precision guide and spacer means penetrates said intervertebral space.

16. In combination, a non-rotatable precision guide and spacer means adapted to be driven into an intervertebral space between two juxtaposed vertebrae of a spine to selectively space opposed surfaces of said juxtaposed vertebrae a predetermined amount, and a quadrilateral tubular osteotome surrounding a portion of said precision guide and spacer means and manipulable to simultaneously cut opposed recesses in the juxtaposed vertebrae while spanning the intervertebral space therebetween, said precision guide and spacer means including guide means for guiding the penetration of said osteotome into said vertebrae, and including stop means controlling the maximum depth to which said osteotome penetrates said vertebrae when driven thereagainst.

* * * * *